US006172610B1

United States Patent
Prus

(10) Patent No.: US 6,172,610 B1
(45) Date of Patent: Jan. 9, 2001

(54) SLEEPING DRIVER DETECTOR AND ALARM SYSTEM

(76) Inventor: Robert S. Prus, 2630 Vermillion Rd., Seabrook, TX (US) 77586

( * ) Notice: Under 35 U.S.C. 154(b), the term of this patent shall be extended for 0 days.

(21) Appl. No.: 09/288,132

(22) Filed: Apr. 8, 1999

(51) Int. Cl.[7] .................................................. G08B 23/00
(52) U.S. Cl. ........................................... 340/575; 340/576
(58) Field of Search .................................... 340/575, 576; 180/272

(56) References Cited

U.S. PATENT DOCUMENTS

| 3,026,503 | * | 3/1962 | Scheer | 340/575 |
| 3,946,288 | * | 3/1976 | Isaksson | 340/575 X |
| 4,359,724 | * | 11/1982 | Zimmerman et al. | 340/575 |
| 5,453,929 | * | 9/1995 | Stove | 340/575 X |
| 5,907,282 | * | 5/1999 | Tuorto et al. | 340/576 |

FOREIGN PATENT DOCUMENTS

| 878 467 | * | 6/1953 | (DE) | 340/575 |
| 2901 865 | * | 7/1979 | (DE) | 340/575 |
| 612 682 | * | 6/1978 | (RU) | 340/576 |
| 757 367 | * | 8/1980 | (RU) | 340/575 |
| 914 360 | * | 3/1982 | (RU) | 340/576 |
| 00785 | * | 2/1985 | (WO) | |
| 15033 | * | 4/1997 | (WO) | |

* cited by examiner

Primary Examiner—Thomas Mullen

(57) ABSTRACT

A sleeping driver detector and alarm system for awaking a sleeping driver. The sleeping driver detector and alarm system includes contacts for measuring skin resistance, a microcontroller for determining a baseline resistance and an alarm that sounds when resistance varies from the baseline. Alternate embodiments provide for the positioning of the contacts integral to the steering wheel of the vehicle or within a glove worn on the hand of a driver. The microcontroller performs a reiterative process to update the baseline resistance and continuously compare the baseline resistance to a current resistance. It is also preferred to include an analog to digital converter for converting analog signals sent from the contacts into a digital signal received by the microcontroller.

10 Claims, 2 Drawing Sheets

SLEEPING DRIVER DETECTOR AND ALARM SYSTEM

BACKGROUND OF THE INVENTION

1. Field of the Invention

The present invention relates to sleep detectors and more particularly pertains to a new sleeping driver detector and alarm system for awaking a sleeping driver.

2. Description of the Prior Art

The use of sleep detectors is known in the prior art. More specifically, sleep detectors heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. 5,585,785; U.S. Pat. No. 5,684,461; U.S. Pat. No. 5,469,143; U.S. Pat. No. 2,199,060; U.S. Pat. No. 3,049,090; and U.S. Pat. No. Des. 365,774.

While these devices fulfill their respective, particular objectives and requirements, the aforementioned patents do not disclose a new sleeping driver detector and alarm system. The inventive device includes contacts for measuring skin resistance, a microcontroller for determining a baseline resistance and an alarm that sounds when resistance varies from the baseline.

In these respects, the sleeping driver detector and alarm system according to the present invention substantially departs from the conventional concepts and designs of the prior art, and in so doing provides an apparatus primarily developed for the purpose of awaking a sleeping driver.

SUMMARY OF THE INVENTION

In view of the foregoing disadvantages inherent in the known types of sleep detectors now present in the prior art, the present invention provides a new sleeping driver detector and alarm system construction wherein the same can be utilized for awaking a sleeping driver.

The general purpose of the present invention, which will be described subsequently in greater detail, is to provide a new sleeping driver detector and alarm system apparatus and method which has many of the advantages of the sleep detectors mentioned heretofore and many novel features that result in a new sleeping driver detector and alarm system which is not anticipated, rendered obvious, suggested, or even implied by any of the prior art sleep detectors, either alone or in any combination thereof.

To attain this, the present invention generally comprises contacts for measuring skin resistance, a microcontroller for determining a baseline resistance and an alarm that sounds when resistance varies from the baseline.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new sleeping driver detector and alarm system apparatus and method which has many of the advantages of the sleep detectors mentioned heretofore and many novel features that result in a new sleeping driver detector and alarm system which is not anticipated, rendered obvious, suggested, or even implied by any of the prior art sleep detectors, either alone or in any combination thereof.

It is another object of the present invention to provide a new sleeping driver detector and alarm system that may be easily and efficiently manufactured and marketed.

It is a further object of the present invention to provide a new sleeping driver detector and alarm system that is of a durable and reliable construction.

An even further object of the present invention is to provide a new sleeping driver detector and alarm system which is susceptible of a low cost of manufacture with regard to both materials and labor, and which accordingly is then susceptible of low prices of sale to the consuming public, thereby making such sleeping driver detector and alarm system economically available to the buying public.

Still yet another object of the present invention is to provide a new sleeping driver detector and alarm system which provides in the apparatuses and methods of the prior art some of the advantages thereof, while simultaneously overcoming some of the disadvantages normally associated therewith.

Still another object of the present invention is to provide a new sleeping driver detector and alarm system for awaking a sleeping driver.

Yet another object of the present invention is to provide a new sleeping driver detector and alarm system which includes contacts for measuring skin resistance, a microcontroller for determining a baseline resistance and an alarm that sounds when resistance varies from the baseline.

Still yet another object of the present invention is to provide a new sleeping driver detector and alarm system that compares a baseline skin resistance to current measurements of skin resistance and sounds an alarm when a predetermined deviation from the baseline is detected.

Even still another object of the present invention is to provide a new sleeping driver detector and alarm system that is integrated into the steering wheel of a vehicle.

Yet still another object of the present invention is to provide a new sleeping driver detector and alarm system that is integrated into a glove worn while driving.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
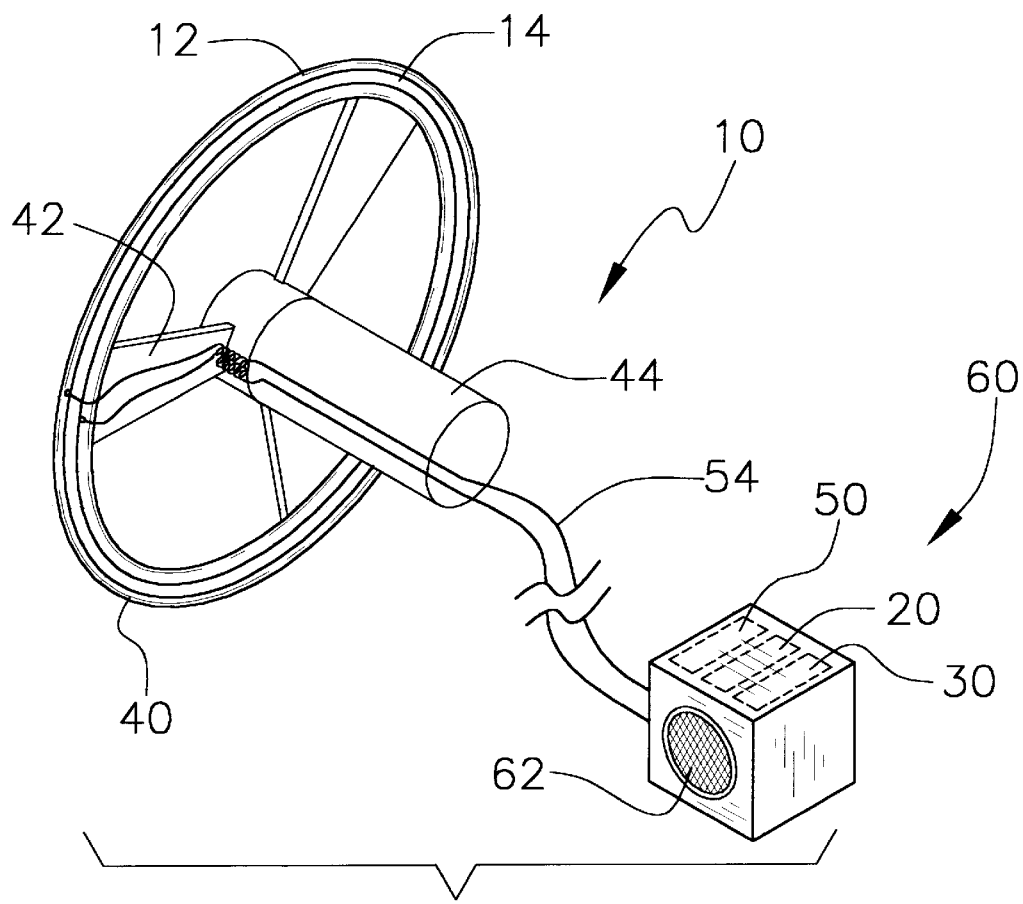
FIG. 1 is a perspective view of a new sleeping driver detector and alarm system according to the present invention.
Figure 2:
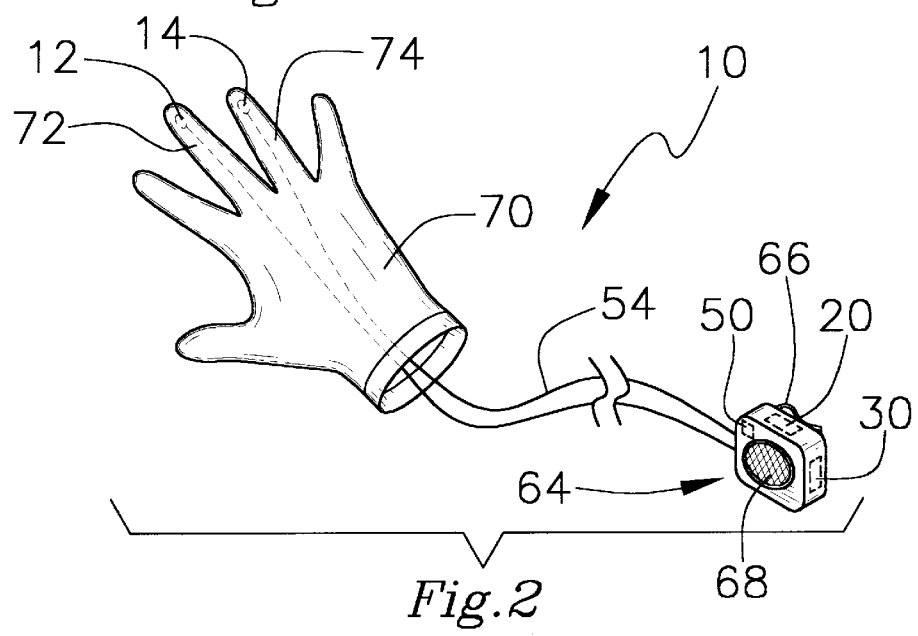
FIG. 2 is a perspective view of the alternate embodiment of the present invention.
Figure 3:
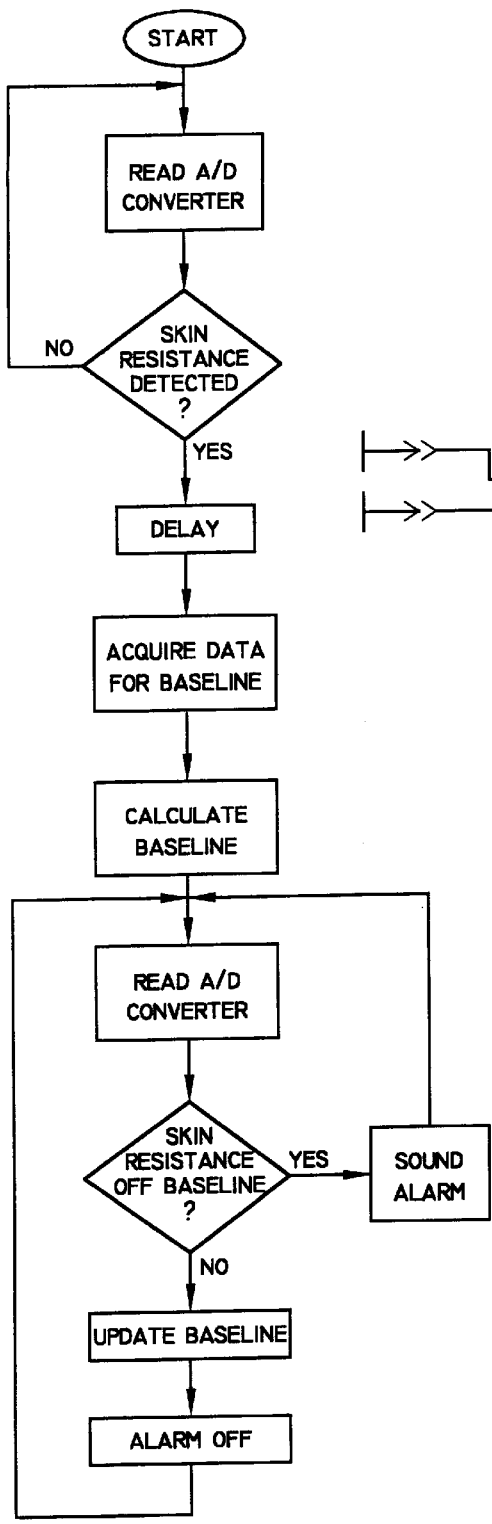
FIG. 3 is a chart of the microcontroller processes of the present invention.
Figure 4:
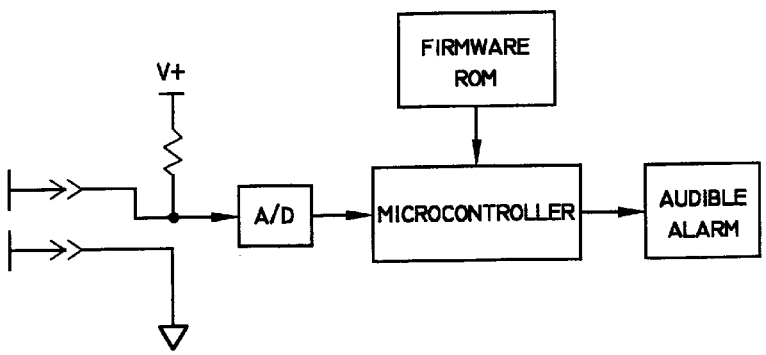
FIG. 4 is a schematic view of the operation of the present invention.
Figure 5:
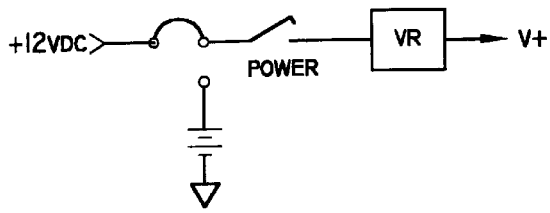
FIG. 5 is a schematic view of the contact circuit of the present invention.

With reference now to the drawings, and in particular to FIGS. 1 through 5 thereof, a new sleeping driver detector and alarm system embodying the principles and concepts of the present invention and generally designated by the reference numeral 10 will be described.

As best illustrated in FIGS. 1 through 5, the sleeping driver detector and alarm system 10 generally comprises a pair of contacts 12 and 14 for measuring skin resistance between two points of a driver's hand. The contacts 12 and 14 are communicatively coupled to a microcontroller 20 designed for determining a baseline skin resistance between the pair of contacts 12 and 14 while the driver is awake. An alarm 30 is operably coupled to the microcontroller 20 such that the microcontroller 20 activates the alarm 30 when a current measurement of the driver's skin resistance varies from the baseline skin resistance by more than a predetermined amount.

In a first embodiment the pair of contacts 12 and 14 are integrally coupled to a steering wheel 40 of a vehicle. One of the pair of contacts 12 is positioned around a circumference of the steering wheel 40 and the other of the contacts 14 is positioned around the circumference of the steering wheel 40 in spaced relationship to the first contact 12. Preferably, the pair of contacts 12 and 14 are positioned on an outer surface of the steering wheel 40 to facilitate skin contact by the driver between the two contacts 12 and 14.

An analog to digital converter 50 is operably connected between the pair of contacts 12 and 14 and the microcontroller 20 for converting analog signals sent from the pair of contacts 12 and 14 to digital signals for processing by the microcontroller 20.

A housing 60 contains the microcontroller 20, converter 50, and the alarm 30. The housing includes a speaker 62 for transmitting the alarm sound.

Preferably, wires 54 extend from the pair of contacts 12 and 14 through a spoke 42 of the steering wheel into a steering column 44 of the steering wheel 40 and into the housing 60.

In the second alternate embodiment, the pair of contacts 12 and 14 are integrally coupled to a glove 70 worn by the driver while driving. The first one of said pair of contacts 12 is positioned at an end of one finger receiving portion 72 of the glove 70. The second one of said pair of contacts 14 is positioned at an end of a second finger receiving portion 74 of the glove 70. Most preferably, the pair of contacts 12 and 14 are positioned on an interior surface of the glove 70 to facilitate skin contact by the driver between the two contacts 12 and 14 when the glove 70 is worn.

The second alternate embodiment further includes a housing 64 having a clip 66 for attaching the housing 64 to the driver. The housing 64 also holds a converter 50, microcontroller 20, and an alarm 30. Most preferably, the housing 64 also includes a speaker 68 for transmitting the alarm sound.

For both embodiments, it is preferred that the microcontroller 20 is programmed to perform the following steps;

determining if a skin resistance from the digital signal from the converter 50 is received, if a signal is not received from the converter 50 then the microcontroller 20 continues to determine if a skin resistance is received from the digital signal from the converter 50;

delaying a predetermined time period when a skin resistance is received from the digital signal from the converter 50;

acquiring data for a baseline value of the skin resistance;

calculating and storing a baseline value for the skin resistance;

receiving a new digital signal from the converter 50;

acquiring data for a current value of skin resistance;

calculating a current value for the skin resistance;

comparing the current value to the baseline value;

activating the alarm 30 when the current value varies from the baseline value by an amount greater than a predetermined acceptable variance; and replacing the baseline value with the current value when a variance between the current value and the baseline value is less than the pre-determined acceptable variance and returning to the step of receiving a new digital signal from the converter 50.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed is:

1. A sleeping driver detector and alarm system comprising:
   a pair of contacts for measuring skin resistance of a driver;
   said contacts being, communicatively coupled to a microcontroller, said microcontroller being for determining a baseline skin resistance between the pair of contacts while the driver is awake;
   an alarm operably coupled to the microcontroller;
   wherein the microcontroller activates the alarm when a current measurement of the driver's skin resistance varies from the baseline skin resistance by more than a pre-determined amount; and
   wherein the pair of contacts are integrally coupled to a steering wheel of a vehicle.

2. The sleeping driver detector and alarm system of claim 1 wherein a first one of the pair of contacts is positioned around a circumference of the steering wheel;
   wherein a second one of the pair of contacts is positioned around the circumference of the steering wheel in spaced relationship to said first one of said pair of contacts; and
   wherein said pair of contacts are positioned on an outer surface of said steering wheel to facilitate skin contact by the driver between the two contacts.

3. The sleeping driver detector and alarm system of claim 2 further comprising:
   a housing containing said microcontroller and said alarm, said housing having a speaker for transmitting said alarm sound; and
   wires extending from said pair of contacts to said microcontroller within said housing, said wires extending from said pair of contacts through a spoke of said steering wheel into a steering column of said steering wheel and into said housing.

4. A sleeping driver detector and alarm system comprising:
   a pair of contacts for measuring skin resistance of a driver;
   said contacts being communicatively coupled to a microcontroller, said microcontroller being for determining a baseline skin resistance between the pair of contacts while the driver is awake;
   an alarm operably coupled to the microcontroller;
   wherein the microcontroller activates the alarm when a current measurement of the driver's skin resistance varies from the baseline skin resistance by more than a pre-determined amount; and
   wherein the pair of contacts are integrally coupled to a glove worn by the driver while driving.

5. The sleeping driver detector and alarm system of claim 4 wherein a first one of said pair of contacts is positioned at an end of one finger receiving portion of said glove;
   a second one of said pair of contacts being positioned at an end of a second finger receiving portion of said glove; and
   wherein said pair of contacts are positioned on an interior surface of said glove to facilitate skin contact by the driver between the two contacts when the glove is worn.

6. The sleeping driver detector and alarm system of claim 5 wherein the first finger receiving portion is adjacently positioned with respect to the second finger receiving portion.

7. The sleeping driver detector and alarm system of claim 5 further comprising:
   a housing having a clip for attaching said housing to said driver, said housing containing said microcontroller and said alarm; and
   said housing further having a speaker for transmitting said alarm sound.

8. A sleeping driver detector and alarm system comprising:
   a pair of contacts for measuring skin resistance of a driver;
   said contacts being communicatively coupled to a microcontroller, said microcontroller being for determining a baseline skin resistance between the pair of contacts while the driver is awake:
   an alarm operably coupled to the microcontroller;
   wherein the microcontroller activates the alarm when a current measurement of the driver's skin resistance varies from the baseline skin resistance by more than a pre-determined amount;
   an analog to digital converter operably connected between said pair of contacts and said microcontroller for converting analog signals sent from said pair of contacts to digital signals for processing by said microcontroller; and
   wherein said microcontroller is programmed to perform the following steps:
   determining if a skin resistance from said digital signal from said converter is received, if a signal is not received from said converter then said microcontroller continues to determine if a skin resistance is received from said digital signal from said converter;
   delaying a predetermined time period when a skin resistance is received from said digital signal from said converter;
   acquiring data for a baseline value of said skin resistance;
   calculating and storing a baseline value for said skin resistance;
   receiving a new digital signal from said converter;
   acquiring data for a current value of skin resistance;
   calculating a current value for said skin resistance;
   comparing said current value to said baseline value;
   sounding an alarm when said current value varies from said baseline value by an amount greater than a pre-determined acceptable variance; and
   replacing said baseline value with said current value when a variance between said current value and said baseline value is less than said pre-determined acceptable variance and returning to said step of receiving a new digital signal from said converter.

9. A sleeping driver detector and alarm system comprising:
   a pair of contacts for measuring skin resistance of a driver;
   said contacts being communicatively coupled to a microcontroller, said microcontroller being for determining a baseline skin resistance between the pair of contacts while the driver is awake;
   an alarm operably coupled to the microcontroller;
   wherein the microcontroller activates the alarm when a current measurement of the driver's skin resistance varies from the baseline skin resistance by more than a pre-determined amount;
   wherein the pair of contacts are integrally coupled to a steering wheel of a vehicle;
   wherein a first one of the pair of contacts is positioned around a circumference of the steering wheel;

wherein a second one of the pair of contacts is positioned around the circumference of the steering wheel in spaced relationship to said first one of said pair of contacts; and wherein said pair of contacts are positioned on an outer surface of said steering wheel to facilitate skin contact by the driver between the two contacts;

an analog to digital converter operably connected between said pair of contacts and said microcontroller for converting analog signals sent from said pair of contacts to digital signals for processing by said microcontroller;

a housing containing said microcontroller and said alarm, said housing having a speaker for transmitting said alarm sound;

wires extending from said pair of contacts to said microcontroller within said housing, said wires extending from said pair of contacts through a spoke of said steering wheel into a steering column of said steering wheel and into said housing; and wherein said microcontroller is programmed to perform the following steps:
  determining if a skin resistance from said digital signal from said converter is received, if a signal is not received from said converter then said microcontroller continues to determine if a skin resistance is received from said digital signal from said converter;
  delaying a predetermined time period when a skin resistance is received from said digital signal from said converter;
  acquiring data for a baseline value of said skin resistance;
  calculating and storing a baseline value for said skin resistance;
  receiving a new digital signal from said converter;
  acquiring data for a current value of skin resistance;
  calculating a current value for said skin resistance;
  comparing said current value to said baseline value;
  sounding an alarm when said current value varies from said baseline value by an amount greater than a predetermined acceptable variance; and
  replacing said baseline value with said current value when a variance between said current value and said baseline value is less than said pre-determined acceptable variance and returning to said step of receiving a new digital signal from said converter.

10. A sleeping driver detector and alarm system comprising:

a pair of contacts for measuring skin resistance of a driver;

said contacts being communicatively coupled to a microcontroller, said microcontroller being for determining a baseline skin resistance between the pair of contacts while the driver is awake;

an alarm operably coupled to the microcontroller;

wherein the microcontroller activates the alarm when a current measurement of the driver's skin resistance varies from the baseline skin resistance by more than a pre-determined amount;

wherein the pair of contacts are integrally coupled to a glove worn by the driver while driving;

wherein a first one of said pair of contacts is positioned at an end of one finger receiving portion of said glove;

a second one of said pair of contacts being positioned at an end of a second finger receiving portion of said glove; and wherein said pair of contacts are positioned on an interior surface of said glove to facilitate skin contact by the driver between the two contacts when the glove is worn;

an analog to digital converter operably connected between said pair of contacts and said microcontroller for converting analog signals sent from said pair of contacts to digital signals for processing by said microcontroller;

a housing having a clip for attaching said housing to said driver, said housing containing said microcontroller and said alarm;

said housing further having a speaker for transmitting said alarm sound; and wherein said microcontroller is programmed to perform the following steps:
  determining if a skin resistance from said digital signal from said converter is received, if a signal is not received from said converter then said microcontroller continues to determine if a skin resistance is received from said digital signal from said converter;
  delaying a predetermined time period when a skin resistance is received from said digital signal from said converter;
  acquiring data for a baseline value of said skin resistance;
  calculating and storing a baseline value for said skin resistance;
  receiving a new digital signal from said converter;
  acquiring data for a current value of skin resistance;
  calculating a current value for said skin resistance;
  comparing said current value to said baseline value;

sounding an alarm when said current value varies from said baseline value by an amount greater than a pre-determined acceptable variance; and replacing said baseline value with said current value when a variance between said current value and said baseline value is less than said pre-determined acceptable variance and returning to said step of receiving a new digital signal from said converter.

* * * * *